(12) United States Patent
Bäck (10) Patent No.: US 7,722,591 B2
(45) Date of Patent: May 25, 2010

(54) HYGIENE PANTS FOR SINGLE USE

(75) Inventor: Lucas Bäck, Billdal (SE)

(73) Assignee: SCA Hygiene Products AB, Gothenburg (SE)

( * ) Notice: Subject to any disclaimer, the term of this patent is extended or adjusted under 35 U.S.C. 154(b) by 164 days.

(21) Appl. No.: 11/847,765

(22) Filed: Aug. 30, 2007

(65) Prior Publication Data

US 2008/0021430 A1   Jan. 24, 2008

Related U.S. Application Data

(63) Continuation of application No. PCT/SE2005/000391, filed on Mar. 2, 2005.

(51) Int. Cl.
 *A61F 13/15* (2006.01)
(52) U.S. Cl. .................. 604/385.31; 604/387
(58) Field of Classification Search ................. 604/358, 604/385.01, 385.03, 385.3, 385.22, 385.24, 604/385.25, 385.27, 385.31, 396; 2/401
See application file for complete search history.

(56) References Cited

U.S. PATENT DOCUMENTS

| | | | |
|---|---|---|---|
| 3,424,162 A * | 1/1969 | Parravicini | 604/396 |
| 3,629,027 A | 12/1971 | Germain | |
| 3,701,710 A | 10/1972 | Germaine et al. | |
| 5,236,430 A | 8/1993 | Bridges | |
| 5,440,764 A | 8/1995 | Matsushita | |
| 5,591,298 A | 1/1997 | Goodman et al. | |
| 5,628,738 A | 5/1997 | Suekane | |
| 5,682,618 A | 11/1997 | Johnson et al. | |

(Continued)

FOREIGN PATENT DOCUMENTS

EP  0 234 658  9/1987

(Continued)

OTHER PUBLICATIONS

Norrby, Copending U.S. Appl. No. 12/279,211, filed Oct. 15, 2008, entitled "Method of Reinforcing a Bond Between Web Materials and an Absorbent Article Comprising Bonded Web Materials".

(Continued)

*Primary Examiner*—Michele Kidwell
(74) *Attorney, Agent, or Firm*—Buchanan Ingersoll & Rooney PC (57) ABSTRACT

Disposable hygiene pants with a front portion (2), a rear portion (3) and a crotch portion (4) provided with two leg openings (5, 6), the longitudinal edge portions (21, 22) of the front portion being connected by longitudinal weld seams (7, 8) to the longitudinal edge portions (31, 32) of the rear portion (3) in order to form a waist opening (9) and the two leg openings (5, 6) in the crotch portion, which leg openings are outwardly delimited in the transverse direction by the inner end portions of the weld seams as seen in the longitudinal direction of the hygiene pants. The hygiene pants have an outer elastic cover (10) and have an absorption unit (11). The cover is made of an elastic laminate having an elastic film applied between two nonwoven layers. The weld seams (7, 8) are each reinforced by at least one nonwoven strip (15, 16) containing thermoplastic fibers and have a tensile strength, in a direction transverse to the weld seam, in excess of 5 N/25.4 mm at least in the portions reinforced with said nonwoven strip (15, 16).

29 Claims, 5 Drawing Sheets

U.S. PATENT DOCUMENTS

| | | | |
|---|---|---|---|
| 5,746,730 | A | 5/1998 | Suzuki et al. |
| 5,769,838 | A | 6/1998 | Buell et al. |
| 5,779,831 | A | 7/1998 | Schmitz |
| 6,042,673 | A | 3/2000 | Johnson et al. |
| 6,240,569 | B1 | 6/2001 | Van Gompel et al. |
| 6,258,077 | B1 * | 7/2001 | Buell et al. ............... 604/393 |
| 6,476,289 | B1 | 11/2002 | Buell et al. |
| 6,585,713 | B1 | 7/2003 | LeMahieu et al. |
| 6,635,135 | B2 | 10/2003 | Kuen et al. |
| 6,652,501 | B2 | 11/2003 | Malchow et al. |
| 6,716,778 | B1 | 4/2004 | Hottner |
| 6,773,527 | B2 | 8/2004 | Campbell et al. |
| 6,837,961 | B2 | 1/2005 | Malchow et al. |
| 7,047,572 | B2 | 5/2006 | Hopkins |
| 2003/0022582 | A1 | 1/2003 | Cree et al. |
| 2003/0065295 | A1 | 4/2003 | Malchow et al. |
| 2003/0069554 | A1 | 4/2003 | Malchow et al. |
| 2003/0120252 | A1 | 6/2003 | Franke et al. |
| 2004/0102757 | A1 | 5/2004 | Olson |
| 2004/0243086 | A1 | 12/2004 | Vangompel et al. |
| 2006/0271009 | A1 | 11/2006 | Cartier et al. |
| 2007/0233034 | A1 | 10/2007 | Hildeberg et al. |
| 2007/0293833 | A1 | 12/2007 | Wennerback |
| 2008/0021430 | A1 | 1/2008 | Back |
| 2008/0033387 | A1 | 2/2008 | Wastlund-Karlsson et al. |
| 2008/0108964 | A1 | 5/2008 | Edwall |

FOREIGN PATENT DOCUMENTS

| | | |
|---|---|---|
| EP | 0 625 346 A1 | 5/1994 |
| EP | 0 875 226 A2 | 11/1998 |
| EP | 0 990 434 A2 | 4/2000 |
| EP | 1 077 055 A2 | 2/2001 |
| EP | 1 035 818 B1 | 4/2002 |
| EP | 1 247 507 A2 | 10/2002 |
| EP | 1 491 105 A1 | 12/2004 |
| FR | 2 873 545 A1 | 2/2006 |
| JP | 10 043235 | 2/1998 |
| WO | WO 94/01069 A1 | 1/1994 |
| WO | WO 99/27876 A1 | 6/1999 |
| WO | WO 02/17843 A2 | 3/2002 |
| WO | WO 03/057469 A1 | 7/2003 |
| WO | WO 03/047488 A1 | 12/2003 |
| WO | WO 2005/122984 A1 | 12/2005 |
| WO | WO 2005/122985 A1 | 12/2005 |
| WO | WO 2006/004637 A1 | 1/2006 |
| WO | WO 2006/038837 A1 | 4/2006 |
| WO | WO 2006/093444 A1 | 9/2006 |
| WO | WO 2007/133127 A1 | 11/2007 |
| WO | WO 2007/133128 A1 | 11/2007 |

OTHER PUBLICATIONS

Edwall et al., Copending U.S. Appl. No. 12/007,662, filed Jan. 14, 2008, entitled "Absorbent Article".

Cartier et al., Copending U.S. Appl. No. 11/441,160, filed May 26, 2006, entitled "Hygiene Pants for Single Use".

Office Action dated Sep. 9, 2008 in Copending U.S. Appl. No. 12/007,662, filed Jan. 14, 2008.

Office Action dated Jul. 31, 2008 in Copending U.S. Appl. No. 11/441,160, filed May 26, 2006.

Office Action dated Oct. 10, 2008 in Copending U.S. Appl. No. 11/441,160, filed May 26, 2006.

Office Action dated Mar. 20, 2009 in Copending U.S. Appl. No. 11/441,160, filed May 26, 2006.

Office Action dated Aug. 2, 2009 in Copending U.S. Appl. No. 11/441,160, filed May 26, 2006.

Englsih translation of Russian Office Action dated Aug. 28, 2009 issued in Russian Federation Application No. 2008136900/14(047345).

* cited by examiner

HYGIENE PANTS FOR SINGLE USE

CROSS-REFERENCE TO RELATED APPLICATIONS

The present application is a continuation of PCT/SE2005/00319, filed on Mar. 2, 2005, and which designates the U.S. The entire contents of PCT/SE2005/000319 are incorporated herein by reference.

TECHNICAL FIELD

The present invention relates to disposable hygiene pants, such as diaper pants, with a longitudinal direction and a transverse direction, comprising, as seen in the longitudinal direction, a front portion, a rear portion and an intermediate crotch portion provided with two leg openings.

BACKGROUND

For hygiene pants, in the form of diaper pants for children and adults and in the form of sanitary towel pants, very high demands are placed on fit and comfort. The hygiene pants must have such elasticity in the transverse direction that they are easy to take off and put on by the user, by a parent or by a care provider. There is also a requirement that they should be soft and textile-like. The hygiene pants, in particular for adult users, must be discrete and they should not be bulky, at least in the areas outside the actual absorption unit. Since they are disposable products, the cost aspect is very important. For cost reasons, the material layers included must be as thin as possible. At the same time, quality and strength requirements must be fulfilled. The hygiene pants, such as diaper pants, must of course resist wear during use. Hygiene pants are exposed to considerable stresses when being put on. The hygiene pants are stretched when they are being pulled over the users hips, and said weld seams are exposed to great stresses. Especially critical areas are the ends of the weld seams at the leg openings or the waist. A break in the weld starts in these critical areas.

In traditional diaper pants, the covers are made up of double nonwovens and of elastic threads lying between these. In the weld seams on this type of cover, there are no fewer than four layers of bonded nonwoven, which gives a sufficiently strong weld seam. The expression bonded nonwoven used here means a nonwoven in which the bonds have not been broken open or weakened in connection with the production of the cover.

Hygiene pants of the type mentioned at the outset have a cover in the form of an elastic laminate composed of an elastic film applied between two nonwoven layers. The weld seams on this type of elastic laminate are affected, in respect of the strength of the seams, by the structure and make-up of the laminate. One object of elastic covers in the form of an elastic film between two nonwoven layers is to give the cover optimal elastic properties at the same time as the fibers in these nonwoven layers give the cover a soft textile feel. The structure of the laminate should therefore be configured such that elastic stretching of the cover is not impeded by the nonwoven layers.

An example of elastic laminates of the type mentioned at the outset is described in WO 03/047488. This publication discloses an elastic laminate composed of an elastic film applied between two nonwoven layers. During production of the elastic laminate, these nonwoven layers have been connected to the film, after which the laminate has been stretched until the bonds in the nonwoven layer have been broken. The elasticity of the laminate is therefore made largely the same as the elasticity of the elastic film. An important disadvantage of this solution is that the weld seams have considerably less strength than the weld seams on said traditional diaper pants.

Other examples of elastic laminates of the type mentioned at the outset are described in the two PCT applications 2004/001004 and 2004/001005. In contrast to the production method according to WO 03/047488, the bonds of the at least one nonwoven layer have not been completely broken open and, instead, the layer has a certain residual strength. The PCT applications 2004/001004 and 2004/001005 describe solutions where elasticity has been combined with softness and with resistance to puncture. In these constructions too, the weld seams are weaker than in said traditional diaper pants.

OBJECT AND SUMMARY

As has been touched on above, a great many demands, some of them contradictory, are placed on disposable hygiene pants. Prior to the present invention, improvements were needed.

By means of the present invention, the problem concerning the risk of the weld seams breaking in hygiene pants of the type mentioned at the outset has been largely reduced or eliminated.

The hygiene pants according to the disclosure are principally characterized in that said weld seams are each reinforced by at least one nonwoven strip containing thermoplastic fibers, which nonwoven strip has been applied to said longitudinal edge portions of the front portion and rear portion of the hygiene pants at least along said inner end portions, as seen in the longitudinal direction of the hygiene pants, of the two edge portions and has there been welded together with said longitudinal edge portions of the cover in order to form said weld seams, and in that the tensile strength of the weld seams, in a direction transverse to the weld seam and in said transverse direction, exceeds 5 N/25.4 mm at least in the portions reinforced with said nonwoven strip, and in that the breaking strength of said cover in the transverse direction exceeds the tensile strength for the reinforced weld seams.

According to one embodiment of the invention, said reinforcing nonwoven strip is applied between the longitudinal edge portions of the front portion and rear portion of the cover.

According to one embodiment, the cover in said longitudinal edge portions of both the front portion and the rear portion, at least along said inner end portions, as seen in the longitudinal direction of the hygiene pants, of the two edge portions has been provided with said reinforcing nonwoven strips, as a result of which the weld seams, at least in their reinforced areas, comprise two layers of said reinforcing nonwoven strips.

According to another embodiment, said nonwoven strip is composed of a single nonwoven strip extending transversely across the hygiene pants. According to one embodiment, the longitudinal direction of the hygiene pants, said single transverse nonwoven strip extends only across said inner end portions of the two edge portions.

Further illustrative embodiments of the hygiene pants according to the present invention are set out in the attached patent claims.

DESCRIPTION OF THE FIGURES

The invention will be described in greater detail below with reference to the attached drawings, in which.

DETAILED DESCRIPTION OF PREFERRED EMBODIMENTS

Figure 1:
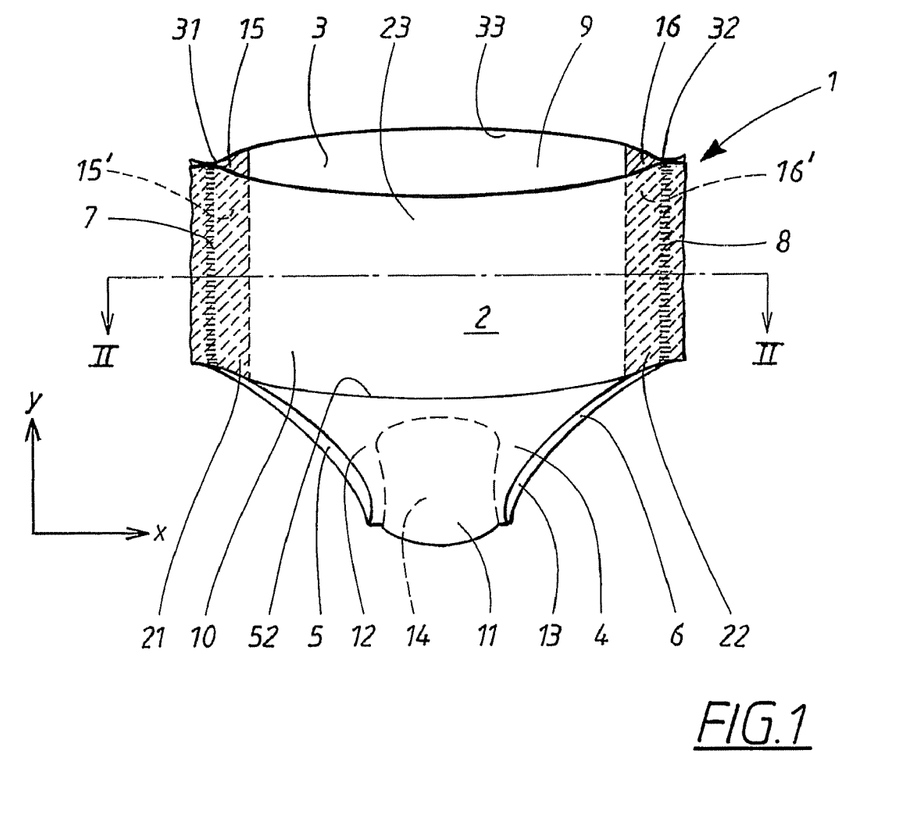
FIG. 1 shows a schematic perspective view of a first illustrative embodiment of hygiene pants according to the invention.

FIG. 1 shows hygiene pants in the form of diaper pants 1 for children or incontinent adults. The diaper pants 1 have a front portion 2, a rear portion 3 and a crotch portion 4 at which leg openings 5, 6 are arranged. The diaper pants have a transverse direction, which in FIG. 1 has been marked with x, and a longitudinal direction, which has been marked with y. The outer longitudinal edge portions 21 and 22 of the front portion, as seen in the transverse direction, are connected by weld seams 7 and 8 to the outer longitudinal edge portions 31 and 32 of the rear portion 3, as seen in the transverse direction, in order to form a waist opening 9, which is delimited by the outer transverse edge portions 23 and 33 of the front portion and rear portion.

The hygiene pants include an outer elastic cover 10 which is composed of an elastic laminate containing an elastic film applied between two nonwoven layers. Elastic laminates suitable for the purpose are described in detail in PCT applications 2004/001004 and 2004/001005. Here, reference is made to the entire content of the two last-mentioned patent applications, both as regards examples of suitable materials for the diaper pants and also as regards illustrative embodiments of the described diaper pants. The laminate is elastic at least in the transverse direction of the diaper pants, i.e. in the x direction in FIG. 1. The elasticity in the x direction should be at least 30%, preferably at least 50%, and most preferably at least 70%, measured according to the elasticity test described in the abovementioned patent applications.

The outer fiber layers in the laminate are intended to provide softness and a textile feel. Examples of suitable materials are carded nonwovens and spunbond nonwovens. The grammage of said fibrous layers is between 10 and 35 g/m2, preferably between 12 and 30 g/m2, and particularly preferably between 15 and 25 g/m2. Examples of suitable fiber materials such as polyethylene and polypropylene are indicated in the abovementioned patent applications.

The elastic film is expediently perforated so that the cover is made permeable to air and vapour. The grammage of the elastic film is expediently between 20 and 100 g/m2, preferably between 20 and 60 g/m2. Suitable examples of materials and material combinations for the elastic film are indicated in abovementioned patent applications 2004/001004 and 2004/001005.

The laminate in the cover 10 can be produced according to a modified version of the method disclosed in WO 03/047488. As has been described in said patent applications 2004/001004 and 2004/001005, the modification is that at least one of the non-elastic nonwoven layers has been stretched under maximum load so that a certain strength is still present in at least one of the nonwoven layers.

Alternatively, the laminate for the cover can also be composed of an elastic laminate which has been produced entirely in accordance with what is described in WO 03/047488. Here, reference is made to the entire content of the last-mentioned patent publication, both as regards examples of suitable materials for the diaper pants and also as regards illustrative embodiments of the described diaper pants.

The term cover designates a framework which supports the pants and which is intended to elastically surround the users trunk and thus support the pants as a whole. In the illustrative embodiment shown in FIG. 1, the cover is composed of the front portion 2 and the rear portion 3. The diaper pants according to FIG. 1 have a crotch portion 4 welded to the cover and in the form of an absorption unit 11. This absorption unit has an outer liquid-tight sheet 12, an inner liquid-permeable sheet 13, and an absorption body 14 arranged between these sheets. The liquid-permeable sheet can, for example, be composed of a nonwoven, such as a spunbond. The outer liquid-tight sheet 12 can, for example, be composed of a thin plastic film, such as a film of polyethylene or polypropylene. The absorption body can, for example, be composed of fluff pulp of cellulose or absorbent foam, possibly in combination with superabsorbent material. Other suitable materials and material combinations for the liquid-tight sheet 12, the absorption body 14 and the liquid-permeable sheet 13 are set out in said patent applications 2004/001004 and 2004/001005.

The hygiene pants according to WO 03/047488 and the hygiene pants according to said patent applications 2004/001004 and 2004/001005 comprise elastic laminates with an elasticity suitable for the intended purpose. This has been achieved by completely or partially breaking open the bonds in at least one of the nonwoven layers surrounding the elastic films in the elastic laminate. An important disadvantage of the nonwoven bonds in the laminate having been completely or partially broken open is, however, that the tensile strength for the weld seams 7 and 8 is weakened considerably compared to the case of traditional diaper pants in which four bonded nonwoven layers have been connected by means of the weld seams. Bonded nonwoven layers here designate nonwovens which have not been broken open or weakened during production of the cover, but which instead retain their tensile strength. In traditional diaper pants, the covers are composed of double nonwovens and of elastic threads lying between them. In the weld seams, therefore, there are no less than four layers of bonded nonwovens, thus providing a sufficiently strong weld seam.

Hygiene pants are subjected to considerable stresses when being put on. The hygiene pants are stretched and the weld seams are exposed to considerable stresses. Especially critical areas are the ends of the weld seams at the leg openings or the waist.

Figure 2:
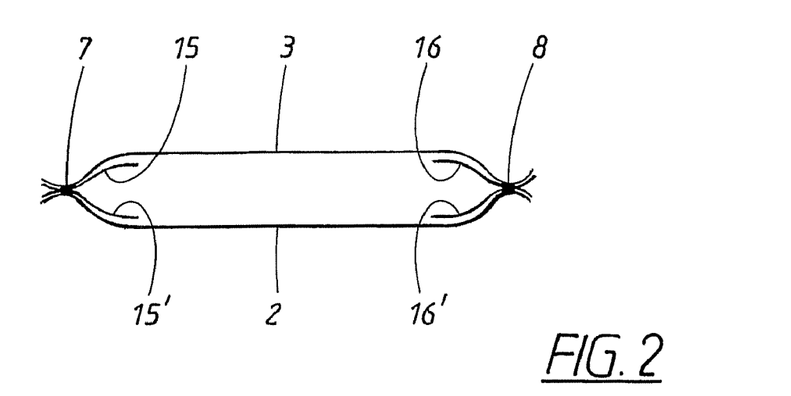
FIG. 2 shows a cross section along line II-II in FIG. 1.

In the embodiment according to FIG. 1, the weld seams 7 and 8 have been reinforced with nonwoven strips 15, 15' and 16, 16', which nonwoven strips have been applied to the inside of the cover along the edge portions 21, 31 and 22, 32, as can clearly be seen from FIG. 2. The nonwoven strips contain thermoplastic fibers which, upon welding of the weld seams, reinforce the latter. The nonwoven strips 15, 16 can, for example, be made of spunbond and are connected to the edge portions of the cover before these are welded together. The reinforcing nonwoven strips have not been stretched such that the fiber bonds have been weakened on application to the edge portions of the cover. When the edge portions are welded together, the reinforcing nonwoven strips therefore retain all of their tensile strength, in contrast to the fiber layers of the elastic material.

Figure 3:
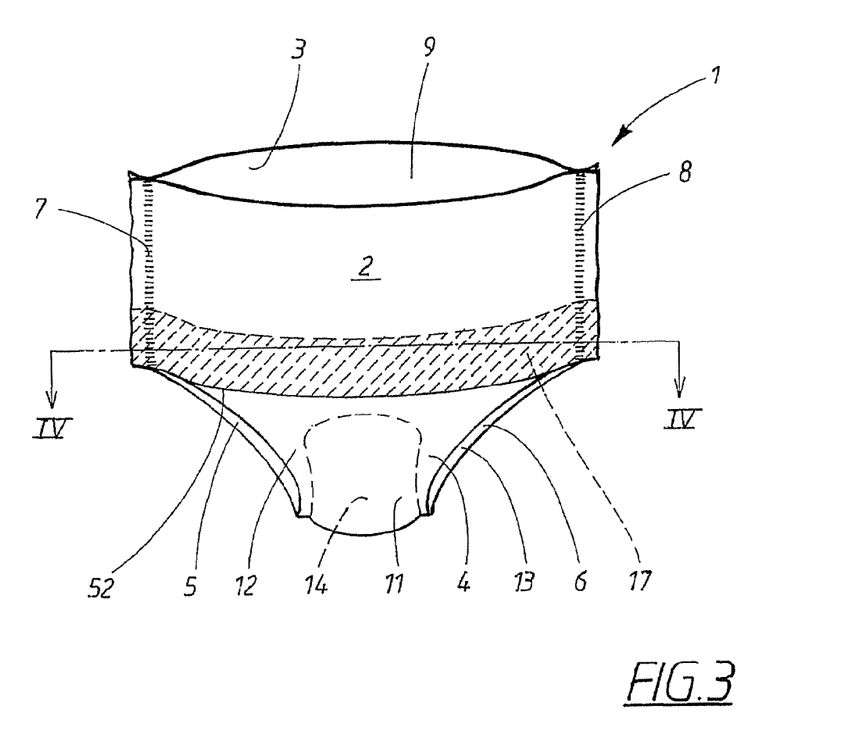
FIG. 3 shows a schematic perspective view of a second illustrative embodiment of hygiene pants according to the invention.
Figure 4:
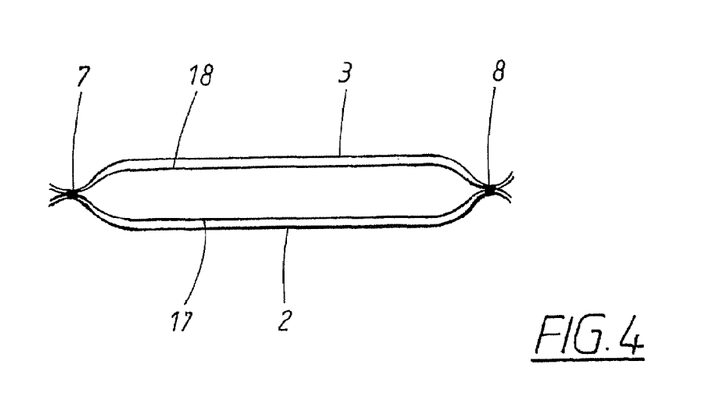
FIG. 4 shows a cross section along line IV-IV in FIG. 3.

As has been mentioned above, the stresses on the weld seams are considerable at the leg openings. In the embodiment shown in FIGS. 3 and 4, two reinforcing strips 17, 18 have been applied to the inside of the cover across the hygiene pants and only across the inner end portions of the end portions of the cover, i.e. at the leg openings. The reinforcing strips 17, 18 are applied, one on the front portion and one on the rear portion, before these portions have been welded together by means of the weld seams to form the cover. In FIGS. 3 and 4, the details corresponding to equivalent details in the illustrative embodiment in FIG. 1 have been provided with the same reference numbers.

Figure 5:
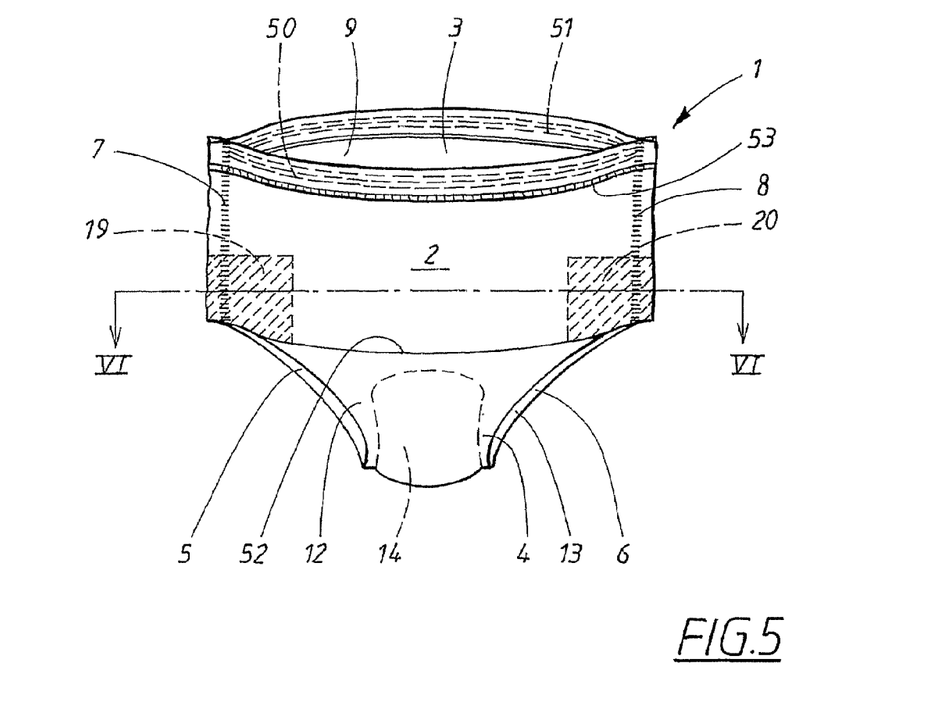
FIG. 5 shows a schematic perspective view of a third illustrative embodiment of hygiene pants according to the invention.
Figure 6:
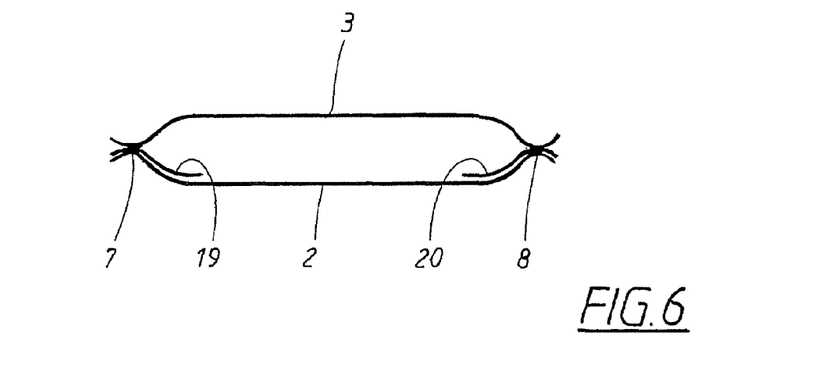
FIG. 6 shows a cross section along line VI-VI in FIG. 5.

FIGS. 5 and 6 show diaper pants where only the edge portions of the cover in immediate proximity to the leg openings have been reinforced with nonwoven strips 19 and 20. In this embodiment, only one strip has been applied inside the front portion of the cover at the leg opening. By the choice of the material used and the choice of grammage, the hygiene pants according to the invention can be configured so that a single reinforcing strip on the front portion, as shown in the embodiment according to FIGS. 5 and 6, provides a sufficiently strong weld seam. The reinforcement of the weld seam is of course the same if the reinforcing strips 19, 20 are applied to the rear portion before welding together. In FIGS. 5 and 6, the details corresponding to equivalent details in the embodiment according to FIGS. 1 and 2 have been provided with the same reference numbers.

In the embodiment according to FIG. 5, the front portion and rear portion of the hygiene pants have been provided with elastic waist bands 50 and 51. These waist bands can expediently be composed of two nonwoven layers with a number of elastic threads applied between the nonwoven layers. The waist bands are connected to the front portion and the rear portion by means of transverse weld joins of which one 53 has been indicated in FIG. 5. When welding together the front portion and rear portion, the waist bands 50 and 51 are welded together by means of the weld seams 7 and 8. By means of the arrangement of the waist bands, the weld seams 7 and 8 are reinforced in the critical portions nearest to the waist opening.

In the illustrative embodiments described above, a cover consisting of the front portion and rear portion of the hygiene pants and with a separate crotch portion has been welded to the rest of the cover by means of a weld which has been indicated by 52 in the drawings. The diaper pants according to FIGS. 1-6 are thus designed with a crotch portion which is substantially non-elastic under the application stresses.

Alternatively, the cover can also comprise the crotch portion, i.e. so that front portion, rear portion and crotch portion are in one piece of elastic material. The absorption unit is applied in this case in the crotch portion inside the cover and connected to the latter, for example by means of melt adhesive.

Figure 7:
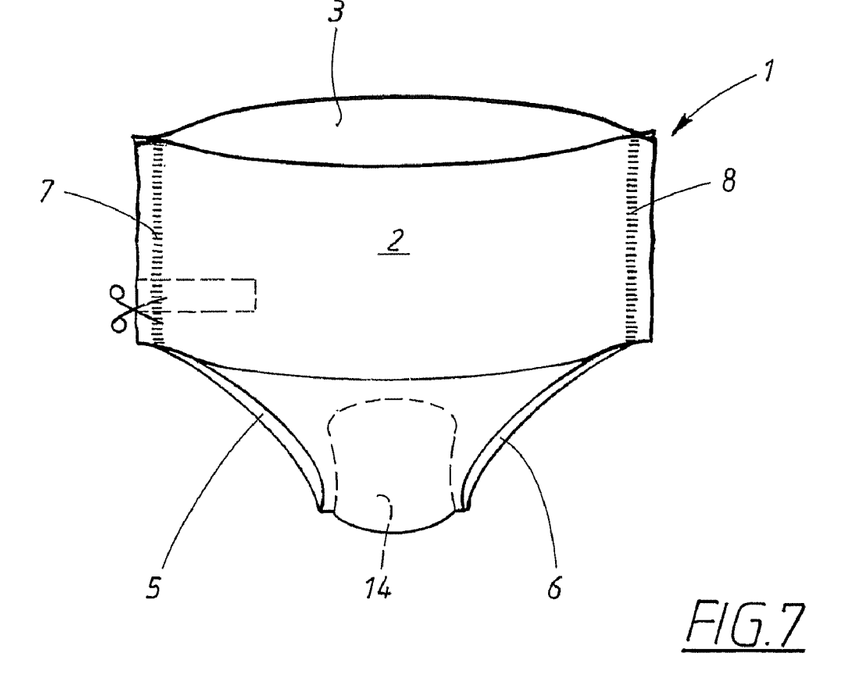
FIGS. 7-9 show, schematically, the method for measuring the weld strength of the hygiene pants.
Figure 8:
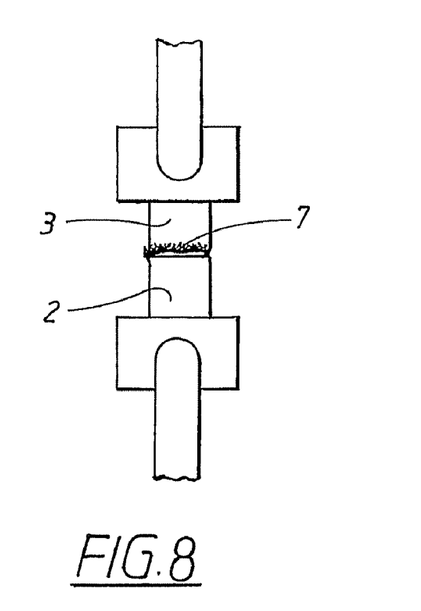
Figure 9:
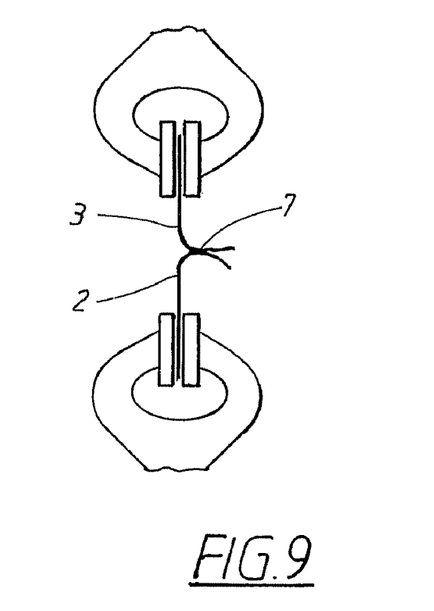

The tensile strength of the weld seams is measured according to the method (reference ASTM D 882) described in patent application PCT 2004/001004. Test specimens are cut from the products, as shown in FIG. 7, in areas which are reinforced with nonwoven strips. The width of the test specimens will be 25.4 mm and the length if possible 50 mm longer than the distance between the clamps on the tensile test instrument Instron 4301. FIGS. 8 and 9 show how the test specimens are secured in the clamps.

To illustrate the effect of the reinforcement of the weld seams by means of nonwoven strips, Table 1 shows the test results for measurements of the tensile strength of a weld seam for connecting two layers of an elastic laminate with and without reinforcement by nonwoven strips. The elastic laminate used in the test specimens comprises an inner elastomeric, three-ply film of PE-SEBS—PE provided with holes and having a grammage of 36 g/m2 and two outer sheets of spunbond nonwoven, polypropylene, which each have a grammage of 22 g/m2. The laminate has been produced according to a modified version of the method described in WO 03/04788. According to the modified version, a spunbond sheet is applied to the film in a tacky state and thus binds to the film, while the other spunbond sheet is adhesively laminated to the film by use of, for example, a pressure-sensitive adhesive (adhesive quantity 3 g/m2). The laminate is stretched gradually until the non-elastic spunbond sheets are stretched to a point less than to the extension at maximum loading in order to maintain some of their strength in the spunbond layers. The elasticity of the laminate after stretching is close to the elasticity of the elastic film.

The abovementioned grammages of the layers concerns the finished material after stretching. Before stretching, the grammages for the individual layers were: inner film 40 g/m2, outer spunbond layer 25 g/m2, and adhesive layer 3 g/m2. Since it is difficult to measure the grammages for individual layers after lamination and stretching, an approximation has been made on the basis of the grammages of the layers before lamination and stretching. The total grammage for the laminate before stretching was 93 g/m2 and after stretching the grammage was 85 g/m2, which corresponds to a deformation of circa 10%. It has been assumed that the deformation of the individual fiber layers and the film is identical, i.e. circa 10%.

The reinforcing nonwoven strips were made of spunbond with a grammage of 20 g/m2. As will be seen from Table 1, the tensile strength for the reinforced weld was 10 N/25.4 mm2 greater than the weld consisting of only two elastic laminates. The result is of course due to the construction of the layers and the grammage. The welding method and weld pattern also affect the strength. The result shown in Table 1 (below) illustrates clearly that a substantial reinforcement of the weld seam is obtained with the aid of reinforcing nonwoven strips.

TABLE 1

|  | Sample | Force at 3% elongation (N) | Force at 5% elongation (N) | Force at 10% elongation (N) | Force at 25% elongation (N) | Maximum force (N) | Elongation at max load (%) | Elongation at max load (mm) |
| --- | --- | --- | --- | --- | --- | --- | --- | --- |
| Elastic/Elastic | 1 | 0.07 | 0.15 | 0.44 | 1.0 | 16.81 | 145 | 73 |
|  | 2 | 0.08 | 0.18 | 0.52 | 1.1 | 15.65 | 108 | 54 |
|  | 3 | −0.01 | 0.00 | 0.32 | 1.0 | 16.12 | 118 | 59 |
|  | 4 | −0.02 | 0.03 | 0.36 | 1.0 | 13.83 | 117 | 58 |
|  | 5 | −0.05 | 0.01 | 0.20 | 0.9 | 12.89 | 114 | 57 |
|  | 6 | 0.07 | 0.17 | 0.50 | 1.2 | 15.46 | 112 | 56 |
|  | 7 | 0.12 | 0.20 | 0.50 | 1.1 | 16.42 | 109 | 55 |

TABLE 1-continued

| | Sample | Force at 3% elongation (N) | Force at 5% elongation (N) | Force at 10% elongation (N) | Force at 25% elongation (N) | Maximum force (N) | Elongation at max load (%) | Elongation at max load (mm) |
|---|---|---|---|---|---|---|---|---|
| | 8 | 0.18 | 0.25 | 0.54 | 1.2 | 17.99 | 107 | 54 |
| | 9 | 0.17 | 0.29 | 0.55 | 1.2 | 22.11 | 117 | 59 |
| | 10 | 0.14 | 0.23 | 0.64 | 1.1 | 17.96 | 110 | 55 |
| | Average | 0.07 | 0.15 | 0.46 | 1.1 | 16.52 | 116 | 58 |
| | SD | 0.08 | 0.10 | 0.13 | 0.09 | 2.54 | 11 | 5.6 |
| | Min | −0.05 | 0.00 | 0.20 | 0.9 | 12.89 | 107 | 54 |
| | Max | 0.18 | 0.29 | 0.64 | 1.2 | 22.11 | 145 | 73 |
| Elastic-NW/NW-Elastic | 1 | 0.07 | 0.13 | 0.60 | 1.7 | 19.38 | 78 | 39 |
| | 2 | 0.05 | 0.13 | 0.61 | 1.6 | 33.63 | 109 | 54 |
| | 3 | 0.07 | 0.26 | 0.68 | 1.7 | 21.26 | 91 | 45 |
| | 4 | 0.06 | 0.15 | 0.52 | 1.2 | 29.17 | 100 | 50 |
| | 5 | 0.06 | 0.21 | 0.56 | 1.5 | 24.70 | 99 | 50 |
| | 6 | −0.03 | 0.01 | 0.31 | 1.1 | 28.23 | 108 | 54 |
| | 7 | 0.10 | 0.19 | 0.51 | 1.2 | 21.49 | 93 | 47 |
| | 8 | 0.09 | 0.13 | 0.35 | 1.1 | 31.56 | 110 | 55 |
| | 9 | 0.05 | 0.14 | 0.46 | 1.1 | 27.57 | 108 | 54 |
| | 10 | 0.16 | 0.22 | 0.55 | 1.3 | 30.58 | 108 | 54 |
| | Average | 0.07 | 0.16 | 0.51 | 1.3 | 26.76 | 100 | 50 |
| | SD | 0.05 | 0.07 | 0.12 | 0.25 | 4.83 | 10 | 5.2 |
| | Min | −0.03 | 0.01 | 0.31 | 1.1 | 19.38 | 78 | 39 |
| | Max | 0.16 | 0.26 | 0.68 | 1.7 | 33.63 | 110 | 55 |

Figure 10:
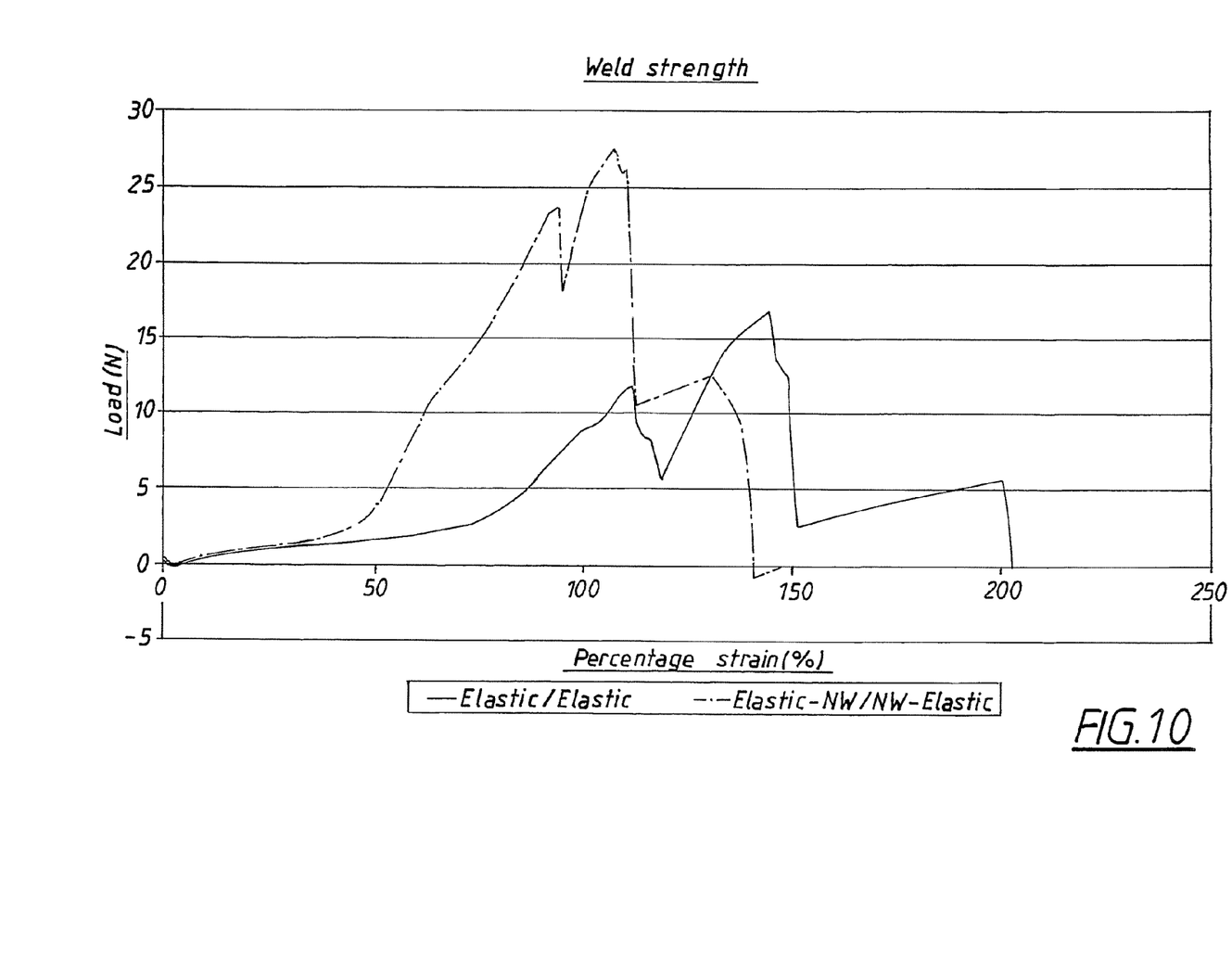
FIG. 10 shows a strain/load diagram to illustrate the change in weld strength with a reinforcement according to the invention.

FIG. 10 shows the stress-strain diagram for the test carried out with the results according to Table 1.

Practical tests show that the tensile strength of the weld seams in a direction transverse to the weld seam should be at least 5 N/25.4 mm, preferably 7 N/25.4 mm and at least 9 N/25.4 mm to ensure that diaper pants of reliable function are obtained. Hygiene pants when used should be able to be easily opened at the weld seams in order to make it easier to take them off. To obtain a reliable function in this respect, it is important that the breaking strength of the cover in the transverse direction exceeds the tensile strength for the reinforced weld seams so that the hygiene pants, when being taken off, do not fall apart in an uncontrolled manner and instead break at the seams. The fact that the reinforcements of the seams can be varied through the choice of nonwoven, the number of layers and the grammage of the reinforcement strips opens up a new possibility of varying the strength of the weld seam. This strength can also be varied through the choice of weld type and weld pattern.

The invention is not limited to the illustrative embodiments described above, and instead a number of modifications are possible within the scope of the attached patent claims, and equivalents thereof. For example, the reinforcement strips do not have to be applied between the elastic laminates and instead the strips can be applied outside two elastic materials which are to be welded together, either outside both laminates or in the form of a single strip outside one of the laminates.

The cover does not need to be made of elastic laminate across the whole front portion and whole rear portion, and instead parts of the front portion and/or rear portion can be made of inelastic material. The important point is that the hygiene pants are sufficiently elastic so that the pants can be put on and taken off with ease. For example, it may suffice for the rear portion to be made of elastic laminate and for the rest of the hygiene pants to be non-elastic.

Alternatively, the hygiene pants can have covers in the form of elastic laminates only in the side portions of the front portion and rear portion, and otherwise have central non-elastic parts along the front portion, rear portion and crotch portion.

The invention claimed is:

1. Disposable hygiene pants, with a longitudinal direction and a transverse direction, the disposable hygiene pants comprising:

a front portion, a rear portion, and an intermediate crotch portion provided with two leg openings, outer longitudinal edge portions of the front portion are connected by longitudinal weld seams to outer longitudinal edge portions of the rear portion to form a waist opening, the waist opening is delimited by outer transverse edge portions of the front portion and of the rear portion, and the two leg openings in the crotch portion are outwardly delimited in the transverse direction by inner end portions of the weld seams as seen in the longitudinal direction of the hygiene pants, and the hygiene pants have an outer elastic cover and an absorption unit which extends in the longitudinal direction across at least part of the crotch portion, and the cover is made of an elastic laminate comprising an elastic film applied between two nonwoven layers, wherein bonds in at least one of the nonwoven layers are completely or partially broken, said longitudinal weld seams are formed at an elastic portion of the elastic laminate and are each reinforced by at least one nonwoven strip containing thermoplastic fibers and wherein the nonwoven strips have not been stretched and thus retain all of their tensile strength, which nonwoven strip has been applied to said longitudinal edge portions of at least one of the front portion and the rear portion of the hygiene pants at least along said inner end portions, as seen in the longitudinal direction of the hygiene pants, of the two edge portions and has there been welded together with said longitudinal edge portions of the cover in order to form said weld seams and the tensile strength of the weld seams, in a direction transverse to the weld seam and in said transverse direction, exceeds 5 N/25.4 mm at least in the portions reinforced with said nonwoven strip, and the breaking strength of said cover in the transverse direction exceeds the tensile strength for the reinforced weld seams.

2. The hygiene pants according to claim 1, wherein said reinforcing nonwoven strip is applied between the longitudinal edge portions of the front portion and rear portion of the cover.

3. The hygiene pants according to claim 1, wherein said reinforcing nonwoven strips are applied along the whole of the longitudinal edge portions.

4. The hygiene pants according to claim 1, wherein each weld seam is reinforced by a single nonwoven strip.

5. The hygiene pants according to claim 1, wherein the cover in said longitudinal edge portions of both the front portion and the rear portion, at least along said inner end portions, as seen in the longitudinal direction of the hygiene pants, of the two edge portions has been provided with said reinforcing nonwoven strips, as a result of which the weld seams, at least in their reinforced areas, comprise two layers of said reinforcing nonwoven strips.

6. The hygiene pants according to claim 1, wherein said nonwoven strip is composed of a single nonwoven strip extending transversely across the hygiene pants.

7. The hygiene pants according to claim 6, wherein in the longitudinal direction of the hygiene pants, said single transverse nonwoven strip extends only across said inner end portions of the two edge portions.

8. The hygiene pants according to claim 1, wherein the cover has an inside which, during use of the pants, is directed towards the user, and an outside, and the nonwoven strip or reinforcing the weld seams is applied to the inside and/or to the outside of the cover.

9. The hygiene pants according to claim 1, wherein said tensile strength across the weld seams in the reinforced portions exceeds 7 N/25.4 mm.

10. The hygiene pants according to claim 1, wherein said tensile strength across the weld seams in the reinforced portions exceeds 9 N/25.4 mm.

11. The hygiene pants according to claim 2, wherein said reinforcing nonwoven strips are applied along the whole of the longitudinal edge portions.

12. The hygiene pants according to claim 2, wherein said nonwoven strip is composed of a single nonwoven strip extending transversely across the hygiene pants.

13. The hygiene pants according to claim 12, wherein in the longitudinal direction of the hygiene pants, said single transverse nonwoven strip extends only across said inner end portions of the two edge portions.

14. The hygiene pants according to claim 1, wherein the cover has an inside which, during use of the pants, is directed towards the user, and an outside, and the nonwoven strip or strips reinforcing the weld seams is applied to the inside of the cover.

15. Disposable hygiene pants with a longitudinal direction and a transverse direction, comprising:
a front portion;
a rear portion;
an intermediate crotch portion provided with two leg openings;
outer longitudinal edge portions of the front portion are connected by longitudinal weld seams to outer longitudinal edge portions of the rear portion to form a waist opening;
the waist opening is delimited by outer transverse edge portions of the front portion and of the rear portion;
the two leg openings in the crotch portion are outwardly delimited in the transverse direction by inner end portions of the weld seams as seen in the longitudinal direction of the hygiene pants;
the hygiene pants having an outer elastic cover;
the hygiene pants having an absorption unit which extends in the longitudinal direction across at least part of the crotch portion;
the cover being made of an elastic laminate comprising an elastic film applied between two nonwoven layers;
bonds in at least one of the nonwoven layers are at least partially broken;
at least one nonwoven strip containing thermoplastic fibers is arranged between the front portion and the rear portion at said longitudinal edge portions of the front portion and the rear portion of the hygiene pants at the weld seams at least along said inner end portions, as seen in the longitudinal direction of the hygiene pants, wherein the nonwoven strips have not been stretched and thus retain all of their tensile strength; and
the nonwoven strip being welded together with said longitudinal edge portions of the cover in order to form said weld seams.

16. The hygiene pants according to claim 15, wherein said reinforcing nonwoven strip is applied along a whole of the weld seams.

17. The hygiene pants according to claim 15, wherein each weld seam is reinforced by a single nonwoven strip.

18. The Hygiene pants according to claim 15, wherein said nonwoven strip is composed of a single nonwoven strip extending transversely across the hygiene pants.

19. The hygiene pants according to claim 15, wherein said tensile strength across the weld seams in the reinforced portions exceeds 5 N/25.4 mm.

20. Disposable hygiene pants with a longitudinal direction and a transverse direction, comprising:
a front portion;
a rear portion;
an intermediate crotch portion provided with two leg openings;
outer longitudinal edge portions of the front portion are connected by longitudinal weld seams to outer longitudinal edge portions of the rear portion to form a waist opening;
an outer elastic cover;
an absorption unit which extends in the longitudinal direction across at least part of the crotch portion;
the cover being made of an elastic laminate comprising an elastic film applied between two nonwoven layers;
bonds in at least one of the nonwoven layers are at least partially broken;
a nonwoven strip containing thermoplastic fibers have been applied to said longitudinal edge portions of the front portion and the rear portion of the hygiene pants at the weld seams of the two edge portions and have been welded together with said longitudinal edge portions of the cover in order to form said weld seams, wherein the nonwoven strips have not been stretched and thus retain all of their tensile strength.

21. The hygiene pants according to claim 20, wherein said reinforcing nonwoven strip is applied between the longitudinal edge portions of the front portion and rear portion of the cover.

22. The hygiene pants according to claim 20, wherein said reinforcing nonwoven strips are applied along the whole of the longitudinal edge portions.

23. The hygiene pants according to claim 20, wherein the cover in said longitudinal edge portions of both the front portion and the rear portion, at least along said inner end portions, as seen in the longitudinal direction of the hygiene pants, of the two edge portions has been provided with said reinforcing nonwoven strips, as a result of which the weld seams, at least in their reinforced areas, comprise two layers of said reinforcing nonwoven strips.

24. The hygiene pants according to claim 20, wherein said nonwoven strip is composed of a single nonwoven strip extending transversely across the hygiene pants.

25. The hygiene pants according to claim 21, wherein said tensile strength across the weld seams in the reinforced portions exceeds 5 N/25.4 mm.

26. The hygiene pants according to claim 1, wherein each of the longitudinal weld seams are reinforced with two nonwoven strips such that the completed seam includes four consecutive nonwoven layers.

27. The hygiene pants according to claim 1, wherein the nonwoven strip has been applied to an outer surface of the elastic laminate forming said longitudinal edge portions of at least one of the front portion and the rear portion of the hygiene pants at least along said inner end portions.

28. The hygiene pants according to claim 15, wherein the nonwoven strip has been applied to an outer surface of the elastic laminate forming said longitudinal edge portions of at least one of the front portion and the rear portion of the hygiene pants at least along said inner end portions.

29. The hygiene pants according to claim 20, wherein the nonwoven strip has been applied to an outer surface of the elastic laminate forming said longitudinal edge portions of at least one of the front portion and the rear portion of the hygiene pants at least along said inner end portions.

* * * * *